(12) United States Patent
Kiani et al.

(10) Patent No.: US 8,473,020 B2
(45) Date of Patent: Jun. 25, 2013

(54) NON-INVASIVE PHYSIOLOGICAL SENSOR COVER

(75) Inventors: Abraham Mazda Kiani, San Juan Capistrano, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 394 days.

(21) Appl. No.: 12/844,720

(22) Filed: Jul. 27, 2010

(65) Prior Publication Data

US 2011/0028811 A1 Feb. 3, 2011

Related U.S. Application Data

(60) Provisional application No. 61/229,682, filed on Jul. 29, 2009.

(51) Int. Cl.
 *A61B 5/02* (2006.01)
(52) U.S. Cl.
 USPC .......................... 600/344; 600/323
(58) Field of Classification Search
 USPC ........................ 600/310, 323, 344
 See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,619,992 A * | 4/1997 | Guthrie et al. | 600/310 |
| 5,632,272 A | 5/1997 | Diab et al. | |

(Continued)

*Primary Examiner* — Clayton E Laballe
*Assistant Examiner* — Leon W Rhodes, Jr.
(74) *Attorney, Agent, or Firm* — Knobbe Martens Olson & Bear, LLP

(57) ABSTRACT

A sensor cover according to embodiments of the disclosure is capable of being used with a non-invasive physiological sensor, such as a pulse oximetry sensor. Certain embodiments of the sensor cover reduce or eliminate false readings from the sensor when the sensor is not in use, for example, by blocking a light detecting component of a pulse oximeter sensor when the pulse oximeter sensor is active but not in use. Further, embodiments of the sensor cover can prevent damage to the sensor. Additionally, embodiments of the sensor cover prevent contamination of the sensor.

17 Claims, 11 Drawing Sheets

U.S. PATENT DOCUMENTS

| | | | |
|---|---|---|---|
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,179,159 B1 * | 1/2001 | Gurley | 221/26 |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Kianl et al. | |
| 6,661,161 B1 | 12/2003 | Lanzo et al. | |
| 6,671,531 B2 | 12/2003 | Al-Ali et al. | |
| 6,671,532 B1 * | 12/2003 | Fudge et al. | 600/344 |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |
| 6,993,371 B2 | 1/2006 | Kiani et al. | |
| 6,996,427 B2 | 2/2006 | Ali et al. | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,015,451 B2 | 3/2006 | Dalke et al. | |
| 7,024,233 B2 | 4/2006 | Ali et al. | |
| 7,027,849 B2 | 4/2006 | Al-Ali | |
| 7,030,749 B2 | 4/2006 | Al-Ali | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,067,893 B2 | 6/2006 | Mills et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,186,966 B2 | 3/2007 | Al-Ali | |
| 7,190,261 B2 | 3/2007 | Al-Ali | |
| 7,190,987 B2 * | 3/2007 | Lindekugel et al. | 600/344 |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |

| | | |
|---|---|---|
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,486,977 B2 * | 2/2009 | Sweitzer et al. .............. 600/323 |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,574,245 B2 * | 8/2009 | Arizaga Ballesteros ...... 600/344 |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| 8,188,433 B2 * | 5/2012 | Gonopolskiy et al. ..... 250/338.1 |

* cited by examiner

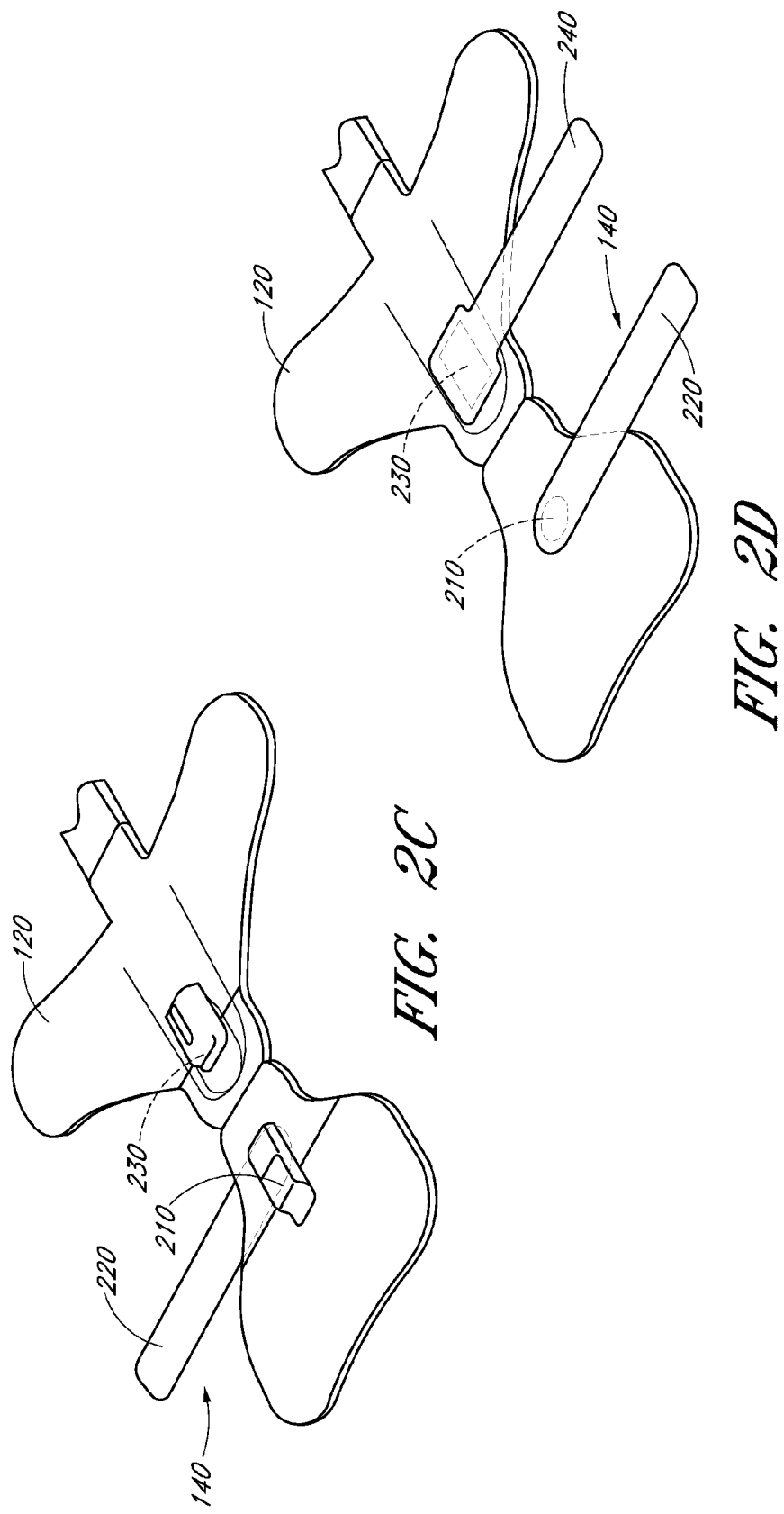

NON-INVASIVE PHYSIOLOGICAL SENSOR COVER

CROSS-REFERENCE TO RELATED APPLICATIONS

The present application claims priority benefit under 35 U.S.C. §119(e) from U.S. Provisional Application No. 61/229,682, filed Jul. 29, 2009, entitled "Non-invasive Physiological Sensor Cover," which is incorporated herein by reference in its entirety.

FIELD OF THE DISCLOSURE

The present invention relates to a sensor for measuring oxygen content in the blood, and, in particular, relates to an apparatus and method for preventing sensor activity when the sensor is not in use.

BACKGROUND OF THE DISCLOSURE

Non-invasive physiological sensors are applied to the body for monitoring or making measurements indicative of a patient's health. One application for a non-invasive physiological sensor is pulse oximetry, which provides a noninvasive procedure for measuring the oxygen status of circulating blood. Oximetry has gained rapid acceptance in a wide variety of medical applications, including surgical wards, intensive care and neonatal units, general wards, and home care and physical training. A pulse oximetry system generally includes a patient monitor, a communications medium such as a cable, and a physiological sensor having light emitters and a detector, such as one or more LEDs and a photodetector. The sensor is attached to a tissue site, such as a finger, toe, ear lobe, nose, hand, foot, or other site having pulsatile blood flow which can be penetrated by light from the emitters. The detector is responsive to the emitted light after attenuation by pulsatile blood flowing in the tissue site. The detector outputs a detector signal to the monitor over the communication medium, which processes the signal to provide a numerical readout of physiological parameters such as oxygen saturation (SpO2) and pulse rate.

High fidelity pulse oximeters capable of reading through motion induced noise are disclosed in U.S. Pat. Nos. 6,770, 028, 6,658,276, 6,157,850, 6,002,952 5,769,785, and 5,758, 644, which are assigned to Masimo Corporation ("Masimo") and are incorporated by reference herein. Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), total Hematocrit (Hct), oxygen concentrations and glucose concentrations, as a few examples. Advanced physiological monitors and corresponding multiple wavelength optical sensors capable of measuring parameters in addition to $SpO_2$, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Laboratories, Inc. and incorporated by reference herein. Further, noninvasive blood parameter monitors and optical sensors including Rainbow™ adhesive and reusable sensors and RAD-57™ and Radical-7™ monitors capable of measuring $SpO_2$, pulse rate, perfusion index (PI), signal quality (SiQ), pulse variability index (PVI), HbCO and HbMet, among other parameters, are also commercially available from Masimo.

SUMMARY OF THE DISCLOSURE

Optical sensors are widely used across clinical settings, such as operating rooms, emergency rooms, post anesthesia care units, critical care units, outpatient surgery and physiological labs, to name a few. In some situations, such as in operating rooms, emergency rooms or critical care units, sensors can be kept attached to monitors to reduce the setup time needed to begin monitoring a patient. While attached, the sensor can generate false readings by detecting ambient light even though the sensor is not in use. The sensor can also cause the monitor to emit alarms or otherwise make noise due to false readings, which can be distracting to medical personnel.

As such, a method and apparatus for preventing false readings are desirable. A sensor cover, according to embodiments of the disclosure, prevents or reduces false readings until the sensor is in use.

Further, in certain embodiments, the sensor cover can prevent damage to the sensor. For example, the sensors cover can protect the emitters and the detector during shipment or prior to use. In certain embodiments, a sensor cover decreases the likelihood of contamination by keeping covered portions of the sensor clean. Sensors in hospitals and other clinical environments are subject to exposure to infectious agents, dust or other foreign matter from depositing on the emitters or detector. The sensor cover can reduce or prevent exposure to these contaminants.

BRIEF DESCRIPTION OF THE DRAWINGS

FIGS. 2A-2C are top cover-attached, top cover-detached, and bottom cover-attached perspective views, respectively, of the sensor cover and sensor of FIG. 1;

FIG. 2D illustrates a first and second sensor covers over the emitters and detector according to an embodiment of the disclosure;

DETAILED DESCRIPTION OF THE PREFERRED EMBODIMENT

A sensor cover according to embodiments of the disclosure is capable of being used with a non-invasive physiological sensor. Certain embodiments of the sensor cover reduce or eliminate false readings from the sensor when the sensor is not in use. Further, embodiments of the sensor cover can prevent damage to the sensor. Additionally, embodiments of the sensor cover prevent contamination of the sensor.

The tissue site of the illustrated embodiments is a finger and the following description therefore refers specifically to the tissue site as a finger for the purposes of clarity. This is not intended to be limiting and, as described herein, the sensor cover of certain embodiments can be used with sensors attachable to other types of tissue sites, such as a toe, ear lobe, nose, hand, foot, forehead or the like.

Figure 1:
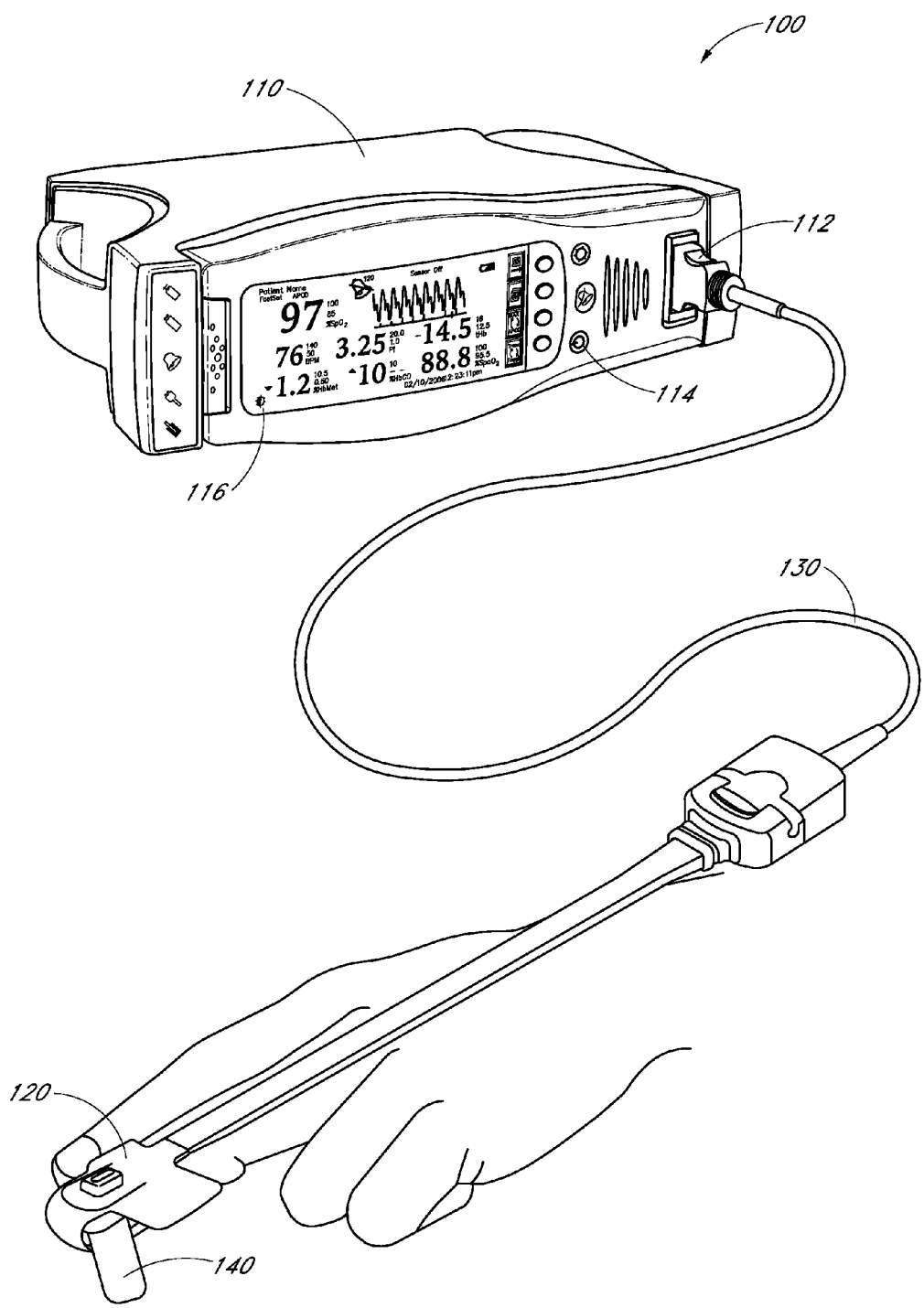
FIG. 1 illustrates a sensor cover attached to a sensor of a physiological measurement system according to an embodiment of the disclosure.

FIG. 1 illustrates an embodiment of a sensor cover attached to a physiological measurement system 100 having a monitor 110 and an optical sensor 120. The optical sensor 120 comprises one or more light emitters and a detector. The optical sensor 120 is configured to plug into a monitor sensor port 112 via a patient cable 130. Monitor keys 114 provide control over operating modes and alarms, to name a few. A display 116 provides readouts of measured parameters, such as oxygen saturation, pulse rate, HbCO, HbMet and Hbt to name a few. Other blood parameters that can be measured to provide important clinical information are fractional oxygen saturation, bilirubin and blood glucose, to name a few.

In the illustrated embodiment of FIG. 1, the sensor cover 140 protrudes outside the sensor. The cover can be made from an opaque material, such as, for example, plastic, polyester, polypropylene, rubber, vinyl, cling vinyl and/or the like. The sensor cover 140 can obstruct the detector and prevent the detector from detecting light, thereby reducing or eliminating false readings. For example, the sensor 120 can sometimes be left attached to a monitor 110 to facilitate quick monitoring of a patient, even when not currently in use. The opaque cover 140 can prevent or reduce false readings caused by the emitters or the ambient light, even if the sensor is active, by preventing the sensor from receiving light. In an embodiment, the opaque material can block all wavelengths of light used by a particular sensor. Other embodiments can block different ranges of wavelengths depending on the type of sensor the cover is used for. In an embodiment, the sensor cover 140 is placed over the emitters to prevent the sensor from emitting light receivable by the detector. In an embodiment, both the detector and emitter are covered.

In some embodiments, the sensor cover 140 can be removed before placement at a measurement site. For example, once a patient arrives, medical personnel can remove the sensor cover 140 and attach the now fully operational sensor 120 to the patient. In some embodiments, the medical personnel can attach the sensor 120 with the cover 140 still in place. The opaque cover prevents measurements from being taken until the sensor 120 is generally secure and the medical personnel are ready to take measurements. For example, movement can generate artifacts for some sensors; therefore waiting until the patient is stable can reduce measurement of inaccurate data. Once the sensor 120 is generally secured to an attachment site, the cover 140 can be removed from the sensor. In some embodiments, the sensor cover 140 can be removed before and/or after placement at a measurement site. The sensor cover 140 can be removed by peeling it off from the sensor or by pulling on the protruding portion.

As will be appreciated by skilled artisans from the disclosure provided herein, various attachment mechanisms can be used. For example, the sensor cover can be attached with an adhesive. In certain embodiments, a restorable adhesive can be used to facilitate reattachments of the sensor cover. The restorable adhesive layer can be rejuvenated by application of alcohol to the adhesive. The cover can then be reattached to the sensor. This can be useful where the sensor is moved to a new location or tissue site because the cover can prevent the sensor from taking false readings while the sensor is moved. In some embodiments, no adhesive is used on the sensor cover to leave no residue. In some embodiments, the sensor cover can be made from static cling vinyl, plastic film, or other "clingy" material with no adhesive used. In some embodiments, the sensor cover can be attached through static electricity allowing the cover to cling to the sensor without any adhesive and/or allowing the sensor cover to be reapplied. In other configurations, the sensor cover can be attached with Velcro, fasteners, tabs, clips, slots, or the like.

As will also be appreciated by skilled artisans from the disclosure provided herein, the sensor cover can be detached in various ways. In some embodiments, the sensor cover can be peeled off from the sensor before the sensor is placed at a measurement site. In some embodiments, the sensor can be pulled off from the sensor after placement by pulling on a protruding portion. Depending on the attachment mechanism, the detachment of the sensor cover can expose an adhesive layer or can leave no adhesive residue on the sensor. In some embodiments, the sensor cover can be unclipped or unhooked.

In certain embodiments, the sensor covers are reusable. For example, the sensor cover can be reused if the sensor is temporarily removed for repositioning or for cleaning. The sensor cover can also be replaced on the sensor when the sensor is no longer in use. In some embodiments, the sensor covers are disposable and are disposed of once removed from the sensor.

Although disclosed with reference to the sensor of FIG. 1, an artisan will recognize from the disclosure herein a wide variety of oximeter sensors, optical sensors, noninvasive sensors, medical sensors, or the like that may benefit from the sensor cover disclosed herein. In various embodiments, the sensor can be adapted to receive a tissue site other than a finger such as a, toe, ear lobe, nose, hand, foot, neck, or other site having pulsatile blood flow which can be penetrated by light from the emitter. In addition, the sensor cover 140 can be used with a portable monitor and associated sensor components in certain embodiments. Such monitors, including the sensor components, can be integrated into a hand-held device such as a PDA and typically do not include cables or separate monitors. Portable monitors are often used by first responders in emergency situations, in part because of their portability and ease of use. As such, sensor covers 140 which can protect the sensor components according to embodiments herein can be of particular benefit when used with spot-check monitors.

Figure 2B:
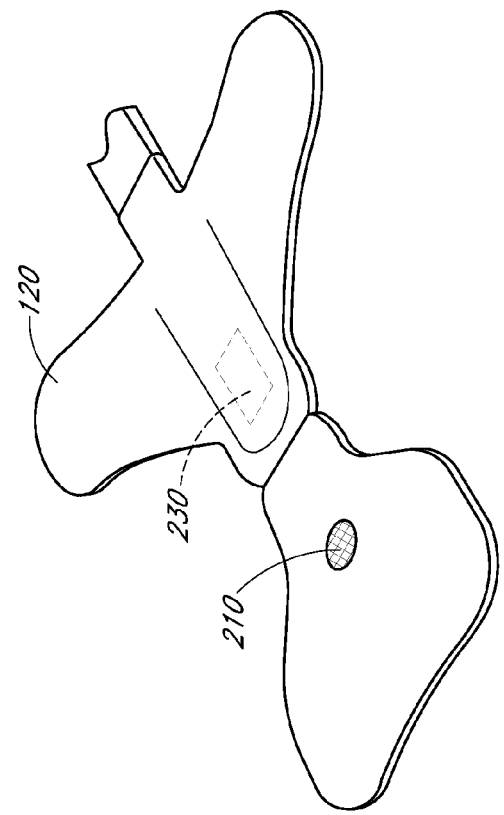
Figure 2A:
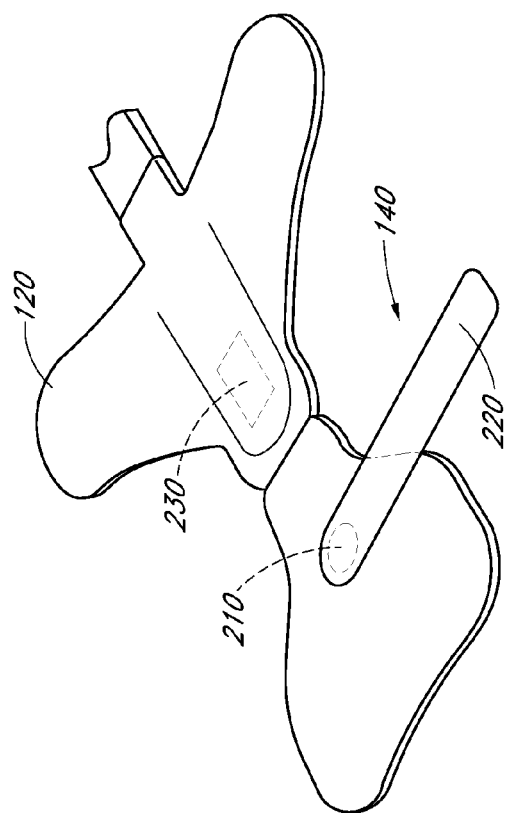

FIGS. 2A-2C are top cover-attached, top cover-detached, and bottom cover-attached perspective views, respectively, of the sensor cover and sensor of FIG. 1. FIG. 2D illustrates a first 140 and second 240 sensor covers placed over the detector 210 and emitters 230, respectively. FIG. 2A illustrates a view of a side of the sensor placed in contact with a tissue site. In FIG. 2A, the sensor cover 140 attaches to the sensor 120 and covers the detector 210, with a protruding portion 220 extending past the sensor. The sensor cover 140 can be a generally elongated shape made of an opaque material. In an embodiment, one side of the sensor cover can include an adhesive layer over the portion of the cover designed to block the detector 210 while the remainder of the cover can be adhesive free. Thus, the cover 140 does not catch on other objects and cause the cover 140 to be prematurely removed. The cover 140 can be removed by pulling on the protruding portion 220 either before or after the sensor 120 has been placed onto a measurement site. FIG. 2B illustrates the sensor 120 with the sensor cover 140 removed. FIG. 2C illustrates a view of an opposite side of the sensor of FIG. 2A.

Figure 3A:
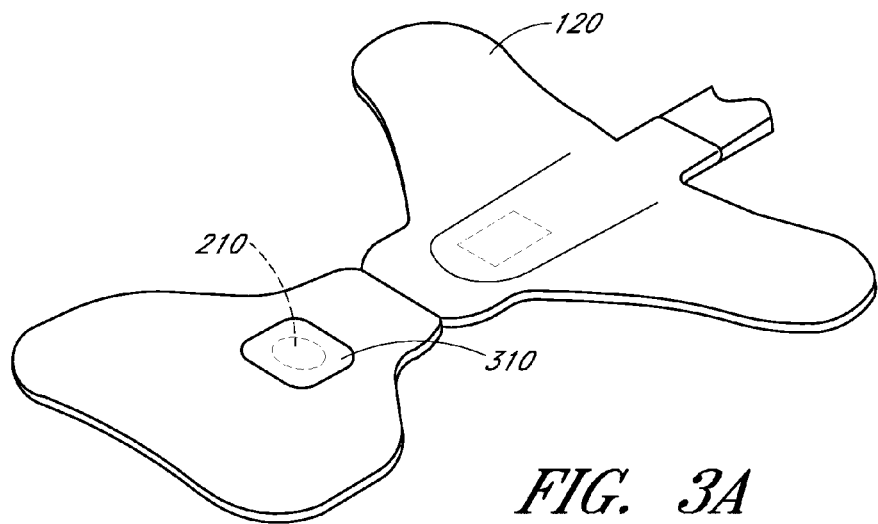
FIG. 3A illustrates a non-protruding sensor cover according to an embodiment of the disclosure.

FIG. 3A illustrates a non-protruding sensor cover 310 according to an embodiment of the disclosure. The opaque sensor cover 310 fits within the sensor 120 and blocks a sensor component 210, such as the emitters or the detector. By staying within the sensor edges, the chance of accidental removal of the cover can be reduced. When the sensor 120 is ready for use, the sensor cover 310 can be removed.

Figure 3B:
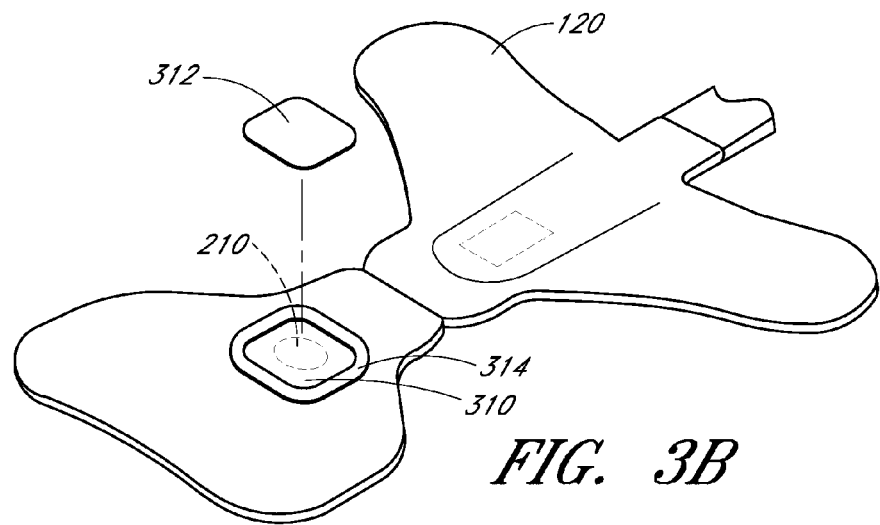
FIG. 3B illustrates a non-protruding sensor cover having an opaque border and a removable opaque center according to an embodiment of the disclosure.

FIG. 3B illustrates a non-protruding sensor cover having an opaque border 314 and a removable opaque center 312. The opaque center 312 can be removed separately from the opaque border 314, leaving an opaque material surrounding the sensor component 210. When the sensor is attached to the patient, the opaque border 314 can minimize light piping, thereby increasing accuracy of the readings. For example, the opaque border 314 can prevent reflected or scattered light that has not passed through tissue from entering into the detector and/or prevent the detector from picking up light from the emitters that fall around instead of on the detector. In an embodiment, the sensor cover can have adhesive on one both sides. Adhesive on both sides of the sensor cover allows the cover to stick to a patient, further preventing light piping or movement of the sensor. In an embodiment the sensor cover can have a clear window section in addition to or instead of a removable center 312.

Figure 3C:
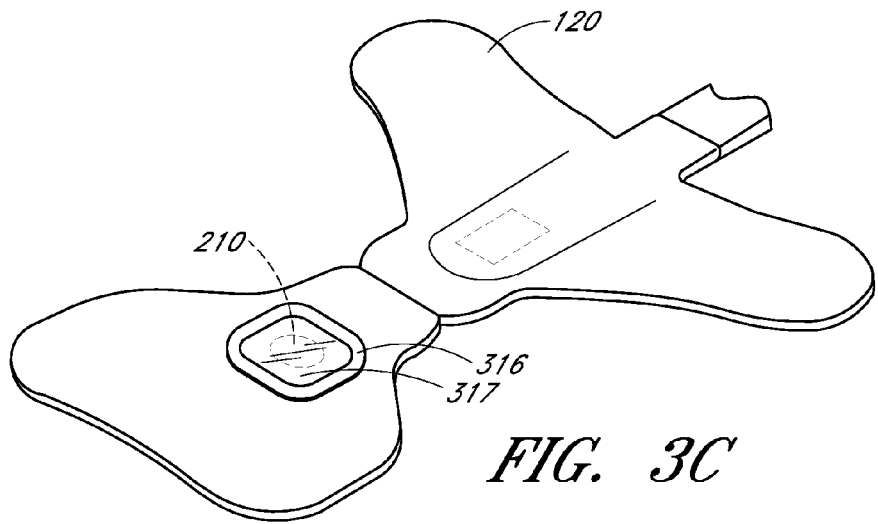
FIG. 3C illustrates a sensor cover having a clear "window" according to an embodiment of the disclosure.

FIG. 3C illustrates a sensor cover 316 having a clear "window" 317 over the sensor component. In an embodiment, the sensor cover can be used to protect the sensor component, provide a new adhesive layer, and/or reduce light piping while allowing the light through the "window." By using a clear window, the sensor cover does not have to be removed when sensor is attached to the patient. In some embodiments, a removable opaque portion can be placed over the window.

Figure 3D:
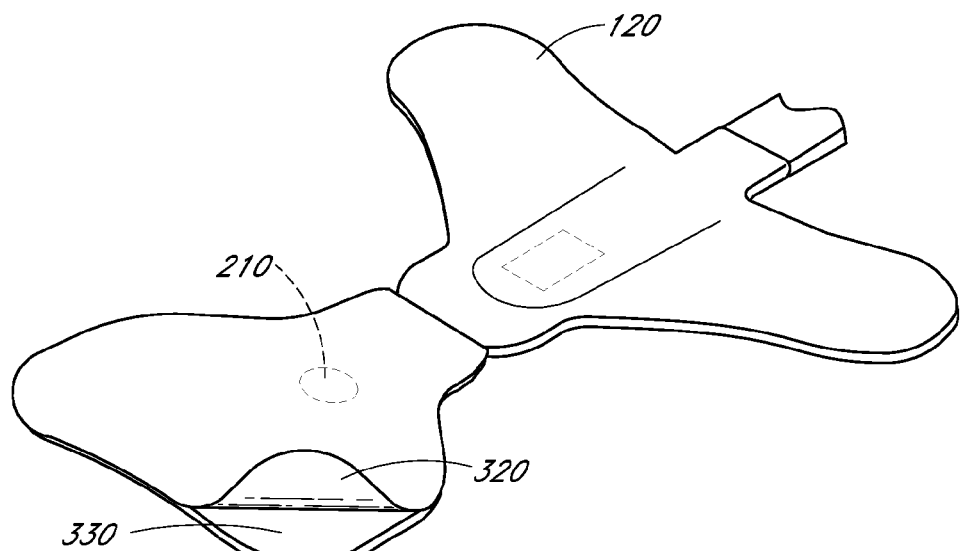
FIG. 3D illustrates a sensor cover integrated with an adhesive cover according to an embodiment of the disclosure.

FIG. 3D illustrates a sensor cover integrated with an opaque adhesive cover 320 for the sensor. An adhesive sensor generally has one or more adhesive covers 320 covering one or more adhesive portions 330 of the sensor. In FIG. 3D, the opaque adhesive cover 320 is extended to cover the sensor component 210. The adhesive cover 320 can be peeled off to reveal the adhesive layer 330 and uncover the sensor component 210.

Figure 3E:
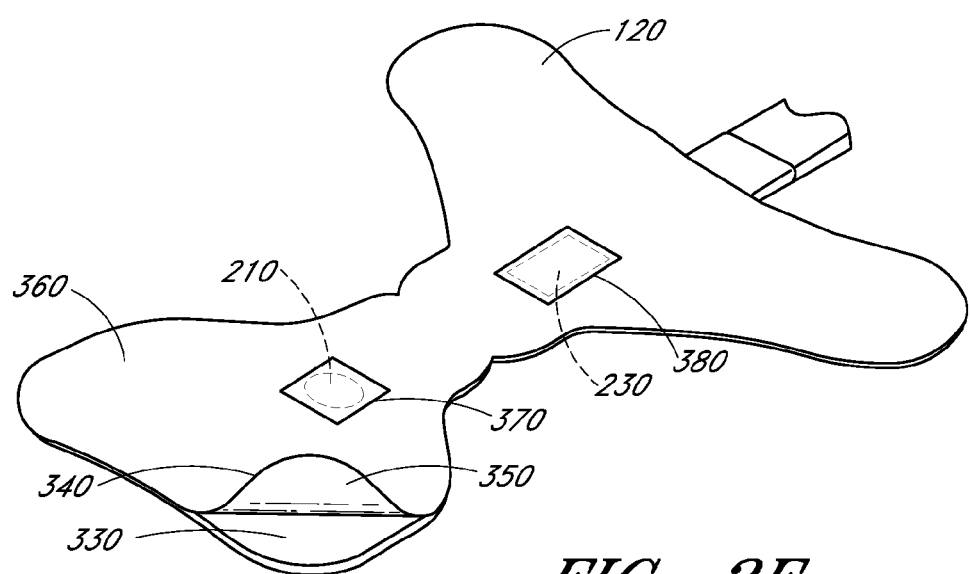
FIG. 3E illustrates a sensor cover covering an adhesive sensor according to an embodiment of the disclosure.

FIG. 3E illustrates a sensor cover 340 covering an adhesive sensor. In FIG. 3E, the opaque sensor cover 340 has adhesive material on both sides of the sensor cover in order to allow reattachment of a sensor where the original adhesive material 330 has lost its adhesiveness. The sensor cover 340 can be placed on the sensor using a first adhesive layer 350 while the sensor is detached from a patient. An adhesive cover (not shown) protects a second adhesive layer 360 and can be removed before the sensor is placed on the patient. The second adhesive layer allows the sensor to be reattached to the patient. The sensor cover can cover both the detector and emitters of the sensor. The sensor cover 322 can have removable or clear sections 370, 380 over the detector and/or emitters to allow light to pass through.

Figure 4A:
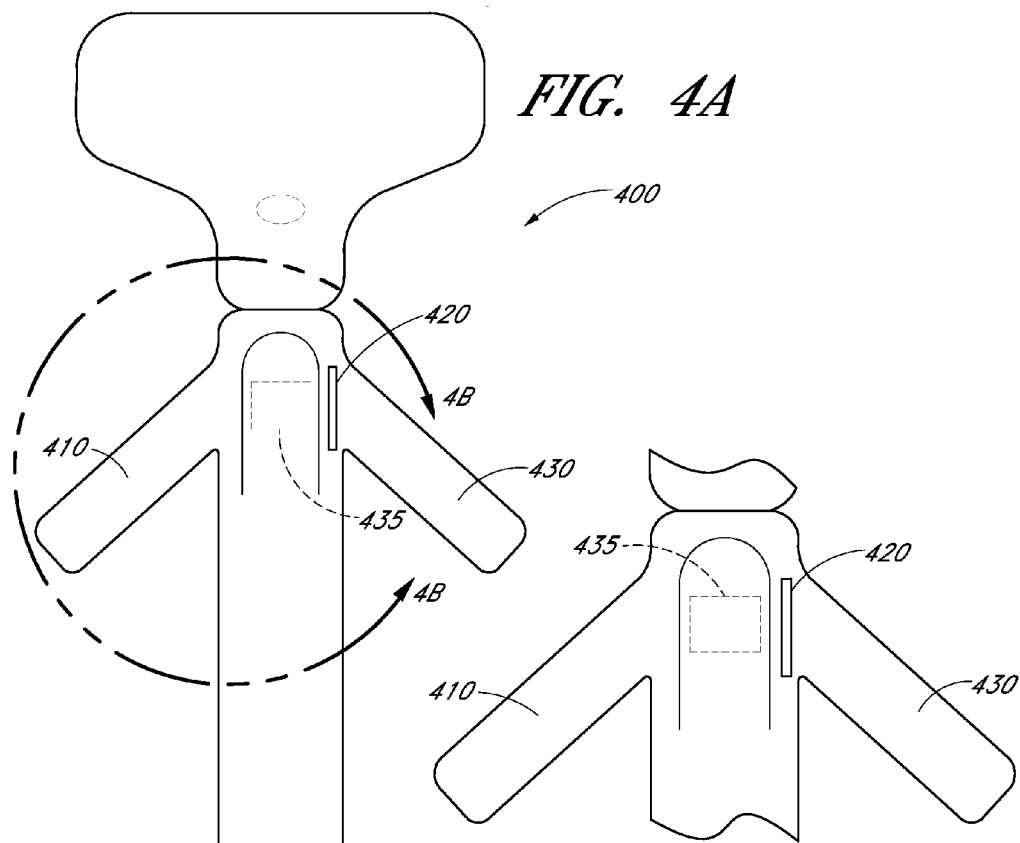
FIGS. 4A-4B are a top view and a close up view, respectively, of an integrated sensor cover according to an embodiment of the disclosure.
Figure 4B:
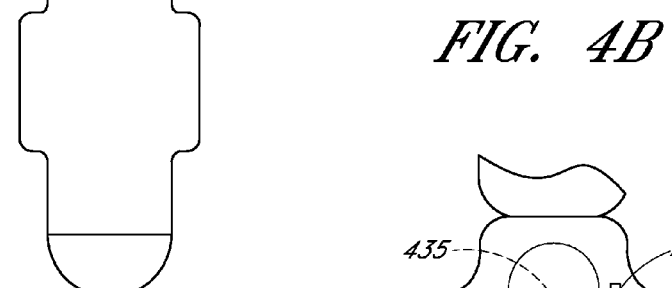
Figure 4C:
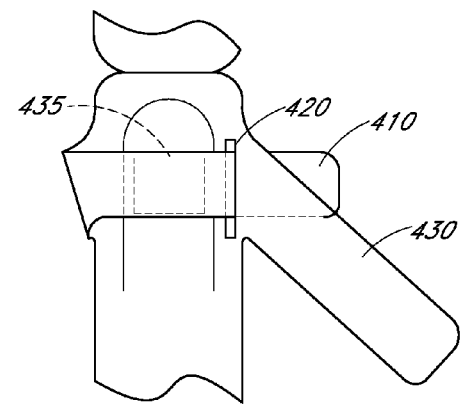
FIG. 4C illustrates the sensor cover of FIGS. 4A-4B covering a sensor component.

FIGS. 4A-4B are a top view and a close up view, respectively, of an integrated sensor cover according to an embodiment of the disclosure. FIG. 4A illustrates an embodiment of the sensor cover where the sensor cover 410 is integrated with the sensor 400. The sensor has a slot 420 positioned near an emitter or a detector. The slot allows an arm 410, 430 to be folded over a sensor component 435, which can be the emitters or the detector, thereby covering it. In certain embodiments, the sensor 400 is an adhesive sensor. The use of a slot allows an adhesive arm 410 to be used as a sensor cover without having to remove the arm's adhesive cover. Once a patient is available, the adhesive arm 410 can be removed from the slot, the adhesive cover can be removed, and the adhesive arms 410, 430 used to secure the adhesive sensor to the patient. FIG. 4B illustrates a close up view of the slot 420 and sensor cover 410 of FIG. 4A. FIG. 4C illustrates the sensor cover 410 folded over the sensor component 435 with the end of the sensor cover inserted into the slot. A portion of the sensor cover extends into the slot and to the back side of the sensor. The slot keeps the sensor cover 410 generally secure against the sensor component 435.

Figure 5A:
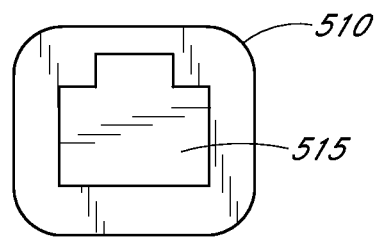
FIG. 5A is a front view a sensor cover attachable to a reusable sensor according to an embodiment of the disclosure.
Figure 5B:
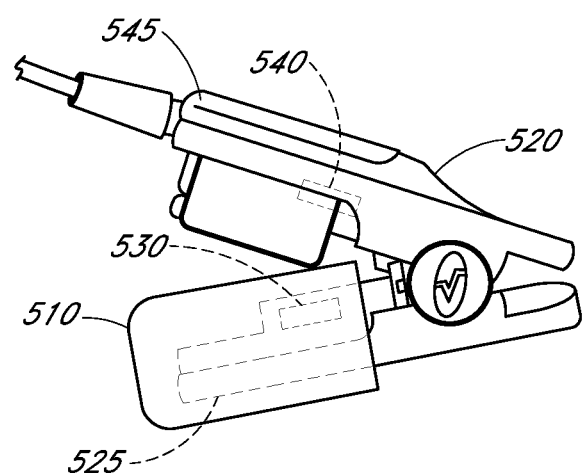
FIG. 5B illustrates the mating of the sensor cover of FIG. 5A with a sensor.

FIG. 5A is a front view a sensor cover 510 attachable to a reusable sensor according to an embodiment of the disclosure. The sensor cover 510 includes a recess 515 into which a sensor housing can be inserted. The sensor housing generally fits closely in the recess 515. Friction between the inner surfaces of the sensor cover 510 and the sensor housing generally secures the housing with the sensor cover 510. FIG. 5B illustrates the mating of the sensor cover 510 of FIG. 5A with a sensor 520. In the illustrated embodiment, the sensor 520 is a reusable clip-style sensor. The sensor cover 510 fits over a lower sensor housing 525. The sensor housings 525, 545 can contain sensor components 530, 540, such as the emitters or the detector. In certain embodiments, the sensor component 530 is a detector and the sensor cover 510 prevents the detector from receiving light. The sensor cover 510 can be removed when the sensor 520 is in use and reattached once the sensor 520 is not in use.

Figure 6:
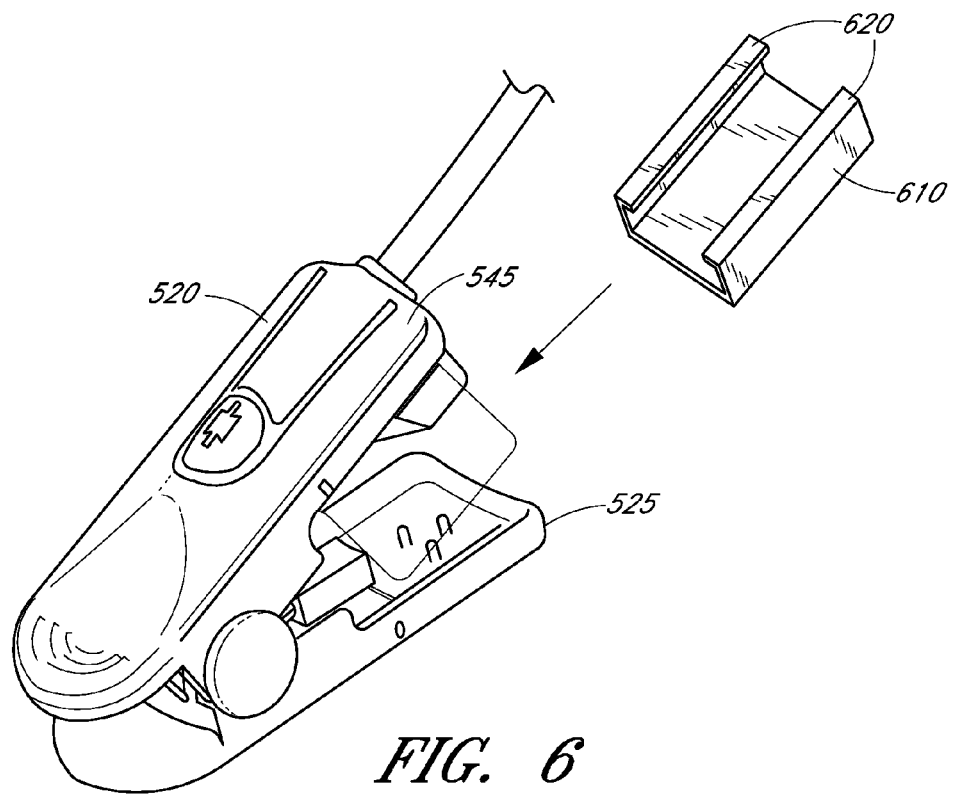
FIG. 6 illustrates a sensor cover attachable to a sensor via one or more tabs according to an embodiment of the disclosure.

FIG. 6 illustrates a sensor cover 610 attachable to a sensor 520 via one or more tabs or attachment arms 620 according to an embodiment of the disclosure. The tabs 620 fit over the sides of an upper housing 545 of the sensor and generally secure the sensor cover 610 against the upper housing 545. The sensor cover 610 covers the sensor component, such as the emitters or the detector, located in the upper housing 545.

Figure 7:
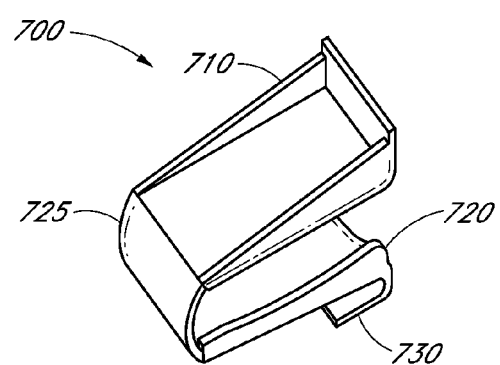
FIG. 7 illustrates a sensor cover configured to block both the emitters and the detector according to an embodiment of the disclosure.

FIG. 7 illustrates an embodiment of the sensor cover 700 configured to block both the emitters and the detector. An upper arm 710 secures against an upper housing of a sensor. A lower arm 720 secures against a lower housing of a sensor. The upper 710 and lower 720 arms are connected by a hinge portion 725. The arms 710, 720 can be attached via a press fit. The lower arm 720 can also include an attachment arm 730 to better secure the sensor cover 700 against the lower housing of the sensor.

Figure 8:
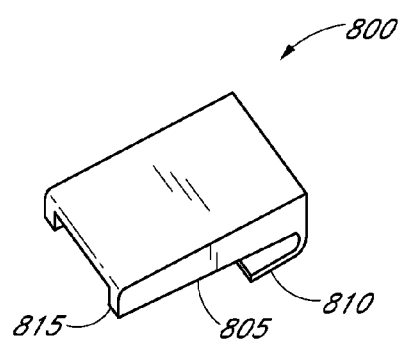
FIG. 8 illustrates a sensor cover attachable to a sensor via an attachment arm according to an embodiment of the disclosure.

FIG. 8 illustrates an embodiment of the sensor cover 800 attachable to a sensor housing via an attachment arm 810. The attachment arm 810 is configured to secure the sensor cover 800 in place when applied to the sensor. Upon application to a sensor, the front portion of the sensor housing may occupy the space defined by the attachment arm 810 and the underside of the lower portion 805 of the sensor cover 800. The attachment arm 810 helps to releasably secure the sensor, via a friction fit, for example. One or more other features, such as the lip 815 disposed on the side of the sensor cover proximal to the sensor can be included to further secure the sensor cover 800 in the sensor. Upon insertion of the sensor cover 800 into the sensor, the sides of the sensor housing abut the lip 815. Accordingly, the lip 815 can help ensure that the sensor cover 800 is positioned appropriately deep within the sensor.

Although the above embodiments have been described with respect to an opaque material intended to optically insulate the optical sensor, as will be appreciated by skilled artisans from the disclosure provided herein, sensor covers made of different insulative materials can be used as appropriate for different types of sensors. For example, sonically insulative materials, such as foam, rubber, cotton, and/or other sound deadening materials can be used to cover sensors that employ sound, such as a bioacoustic or ultrasound sensor. In some embodiments, electrically insulative materials, such as rubber, polyethylene, silicone and/or other insulators can be used to cover sensors that employ electrical signals, such as bio-impedance sensors. In some embodiments, mechanically insulative materials, such as hard plastic, metal, rubber, silicone, and/or other rigid or dampening materials can be used to cover mechanical sensors to prevent sensor actuation. In some embodiments, chemically insulative material, such as plastic, metal, polyethylene or the like can be used to cover chemical sensors and prevent their exposure to the environment.

Figure 9B:
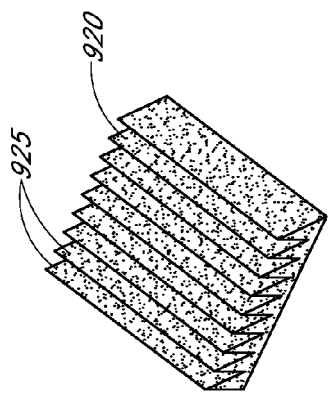
FIGS. 9A-9D illustrates embodiments of the sensor covers configured for attachment to a bioacoustic sensor, according to embodiments of the disclosure.
Figure 9A:
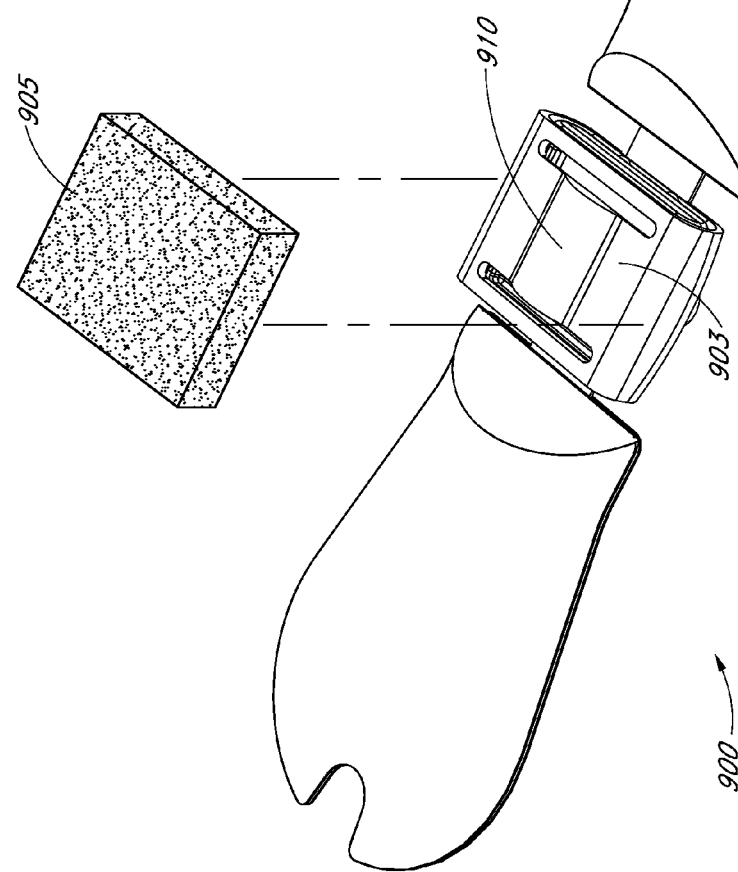

FIGS. 9A-9D illustrate embodiments of sensor covers for a bioacoustic sensor. FIG. 9A illustrates one embodiment of a bioacoustic sensor. The bioacoustic sensor 900 is configured for placement against a patient's skin. The contact surface 903 of the sensor 900 is placed against the skin. The bioacoustic sensor picks up sound waves from the patient's body and converts them into electrical signals for transmission to a monitoring device. In one embodiment, the bioacoustic sensor can use a piezoelectric transducer as the sensing element to detect sound waves. In FIG. 9A a sensor cover 905 made of a sound-deadening material, such as foam, rubber, and/or cotton, is attached to the contact surface to prevent sound waves from being detected by the bioacoustic sensor 900. The sound-deadening material can be attached by adhesive, tabs, clips, friction fit, and/or other connection mechanism. In FIG. 9A, the bioacoustic sensor has a bump 910 on the contact surface 903 positioned to apply pressure to the sensing element so as to bias the sensing element in tension and improve the receptivity of the sensing element to sound waves. Where such a bump 910 exists on the contact surface 903 of the sensor, embodiments of sensor cover 905 can be provided with a corresponding recess.

FIG. 9B illustrates an embodiment of the sensor cover 920 made of shaped sound-deadening material to increase the surface area available to absorb sound. In one embodiment, a plurality of wedge shaped protrusions 925 is formed on the surface of the sensor cover 920. In other embodiments, different shaped protrusions can be used, such as waveform, pyramid, egg crate, and/or other shapes to increase the surface area.

Figure 9C:
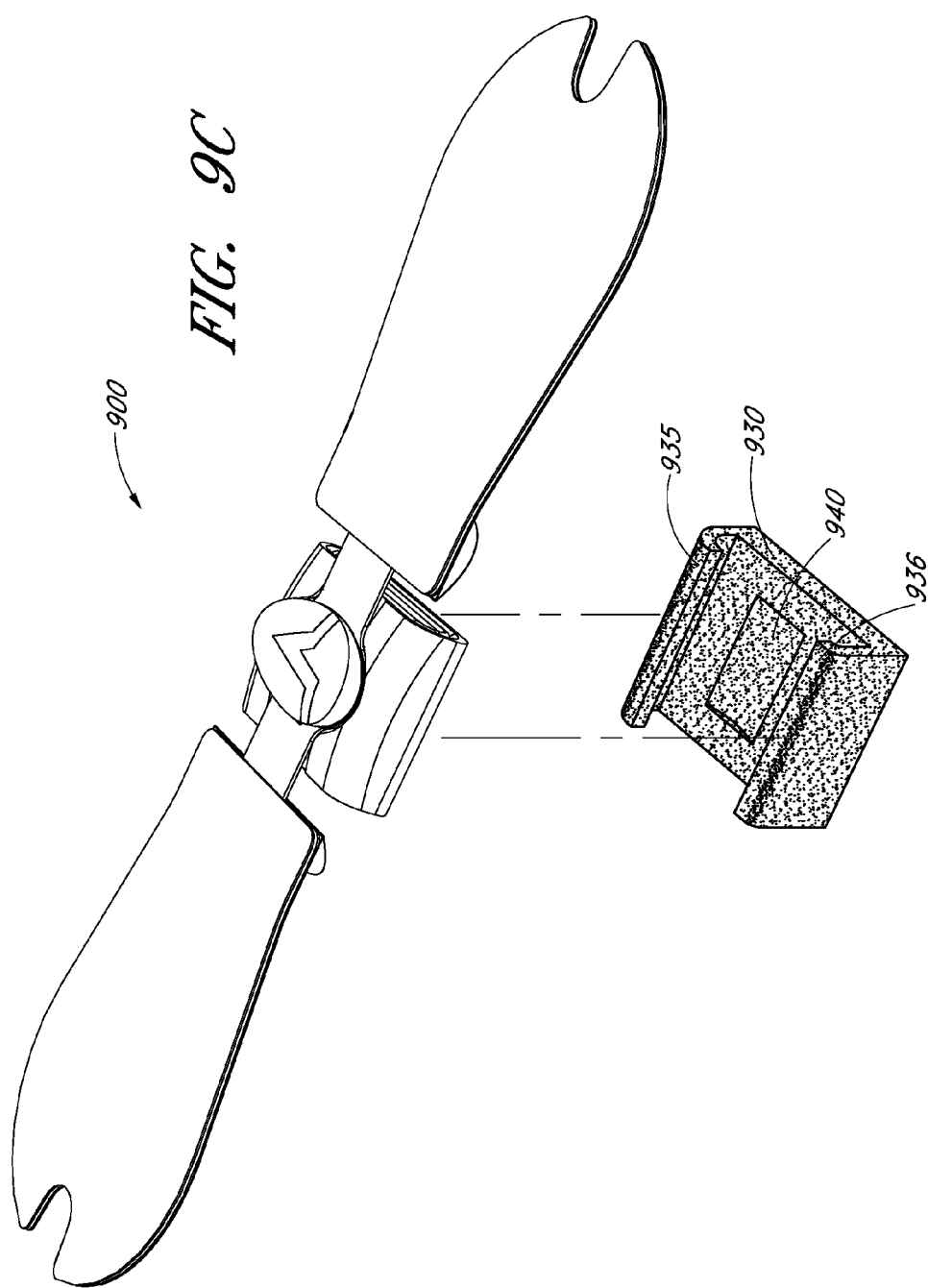

FIG. 9C illustrates a bioacoustic sensor cover having one or more attachment arms according to an embodiment of the disclosure. An attachment arm 935 is configured to releasably secure the sensor cover 930 when applied to the sensor via a friction fit, for example. A second attachment arm 936 can be provided to further secure the sensor cover 930 to the sensor 900. A recess 940 can also be formed on the interior surface of the sensor cover 930 in order to conform to protrusions on the contact surface of the sensor 900. Where the contact surface of the sensor 900 is flat, the interior surface can also be flat.

Figure 9D:
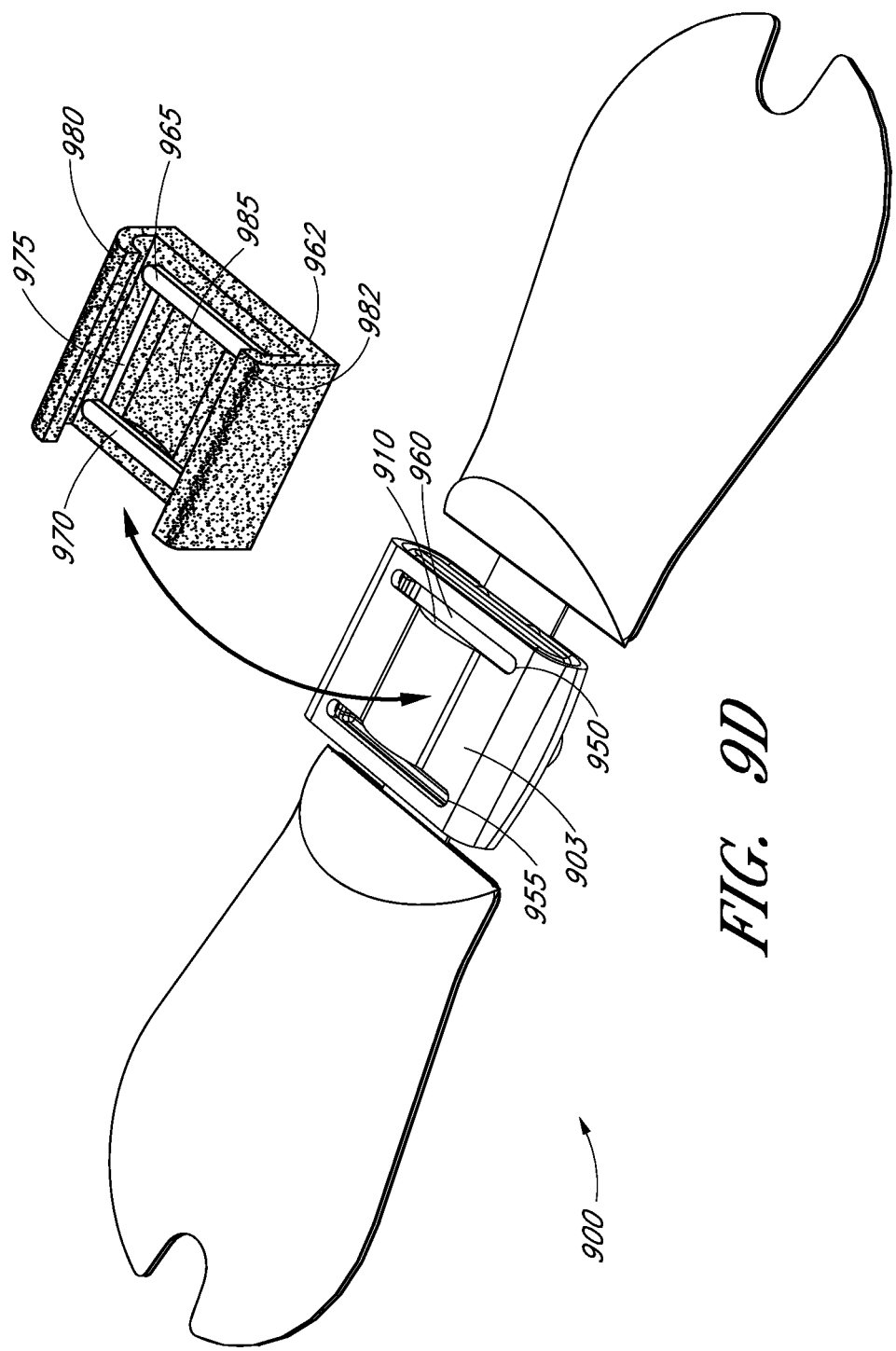

FIG. 9D illustrates a bioacoustic sensor having conductive leads according to an embodiment of the disclosure. In FIG. 9D, the illustrated bioacoustic sensor 900 has one or more apertures 950, 955 exposing the sensing element 960 to the contact surface 903. In one embodiment, the sensor cover 962 prevents the bioacoustic sensor from taking readings by creating an electrical short in the sensor. One or more conductive leads or wires 965, 970 configured to fit into the apertures 950, 955 in the sensor housing are disposed on the sensor cover 962. The conductive leads 965, 970 abut the negative and positive electrical poles of the sensing element 960. The conductive leads can be formed of copper or other conductive material. In one embodiment, the conductive leads 965, 970 can abut internal wiring that connects to the negative and positive electrical poles, such that a direct connection is not required. The conductive leads 965, 970 are joined by a connector lead or wire 975 to generate a short circuit in the sensor 900. In an embodiment, the conductive leads 965, 970 and connector lead 975 are a single connected structure. In an embodiment, the sensor cover 962 further comprises one or more attachment arms 980, 982 for releasably securing the sensor cover 962 to the sensor 900. In an embodiment, the sensor cover 962 further comprises a recess 985 to conform against a protrusion 910 on the contact surface 903 of the sensor. In one embodiment, the sensor cover 962 is formed out of a sound deadening material, such as foam or rubber. In one embodiment, the sensor cover 962 is made of hard plastic or other types of plastic materials.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Various sensor covers have been disclosed in detail in connection with various embodiments. These embodiments are disclosed by way of examples only and are not to limit the scope of the claims that follow. One of ordinary skill in the art will appreciate the many variations, modifications and combinations. For example, in various embodiments, adhesive, snap-fit, friction-fit, clips, tabs, and other attachment mechanisms can be employed. In addition, in various embodiments the sensor covers are used with a sensor that can measure any type of physiological parameter. In various embodiments, the sensor covers can be for any type of medical device or sensor. In various embodiments, adhesive can be placed on both sides of the sensor cover to aid in the reattachment of sensors where the sensor adhesive has grown weak. In various embodiments, sensors covers can be made in whole or in part of materials such as foam, polyester, polypropylene, rubber, vinyl, cling vinyl, urethane rubber plastic or other plastic materials, cloth, metal, combinations of the same or the like.

What is claimed is:

1. A sensor covering system for a noninvasive physiological sensor, the sensor covering system comprising:
   a noninvasive physiological sensor comprising sensing components including a light-emitting component and a light-detecting component; and
   a sensor cover comprising:
   an opaque substrate;

a first adhesive layer formed on a first side of the opaque substrate, the first adhesive layer configured to attach to the noninvasive physiological sensor; and a second adhesive layer formed on a second side of the opaque substrate, the second adhesive layer configured to attach to a tissue site;

wherein, in a first configuration, the sensor cover covers at least one of the sensing components while the noninvasive physiological sensor is active, the sensor cover preventing measurement of one or more physiological parameters by the noninvasive physiological sensor in the first configuration;

wherein the removal of at least a portion of the sensor cover in a second configuration allows the noninvasive physiological sensor to actively measure the one or more physiological parameters in the second configuration.

2. A sensor covering system for a noninvasive physiological sensor, the sensor covering system comprising:

a noninvasive physiological sensor comprising sensing components including a light-emitting component and a light-detecting component; and a sensor cover comprising:

an opaque substrate;

a first adhesive layer formed on a first side of the opaque substrate, the first adhesive layer configured to attach to the noninvasive physiological sensor;

a window formed on the opaque substrate, the window aligned over the light-detecting component of the noninvasive physiological sensor, wherein the window allows light to reach the light-detecting component; and an opaque adhesive cover, wherein the adhesive cover overlays the first adhesive layer and the window, the opaque adhesive cover preventing the light detecting component from detecting light in the first configuration;

wherein, in a first configuration, the sensor cover covers at least one of the sensing components while the noninvasive physiological sensor is active, the sensor cover preventing measurement of one or more physiological parameters by the noninvasive physiological sensor in the first configuration;

wherein the removal of at least a portion of the sensor cover in a second configuration allows the noninvasive physiological sensor to actively measure the one or more physiological parameters in the second configuration.

3. The sensor covering system of claim 2, wherein the removable portion of the sensor cover in the second configuration comprises the opaque adhesive cover.

4. The sensor covering system of claim 2, wherein the window comprises a light-permeable material.

5. The sensor covering system of claim 2, wherein the window comprises a cutout of the opaque substrate.

6. A sensor cover for use with a noninvasive physiological sensor, the sensor cover comprising:

an opaque portion attachable over a sensing portion of the sensor, the opaque portion preventing the sensing portion from measuring a physiological variable; and a connector for attaching the sensor cover to a sensor;

wherein the sensor is an adhesive sensor having a flexible substrate and an adhesive layer;

wherein the opaque portion is integrated with an adhesive cover, the adhesive cover attachable to the adhesive layer of the sensor.

7. The sensor cover of claim 6, wherein the connector comprises an adhesive layer on the opaque portion attachable over the sensing portion of the sensor.

8. The sensor cover of claim 6, further comprising an elongate portion extending past the sensor, the elongate portion facilitating removal of the sensor cover.

9. The sensor cover of claim 6, wherein the connector comprises a surface of the cover frictionally engageable with the sensor.

10. The sensor cover of claim 6, wherein the sensor is at least one of a pulse oximeter sensor, a bioacoustic sensor, and a bioimpedance sensor.

11. The sensor cover of claim 6, wherein the sensor is a clip-type sensor.

12. A sensor cover for use with a noninvasive physiological sensor, the sensor cover comprising:

an opaque portion attachable over a sensing portion of the sensor, the opaque portion preventing the sensing portion from measuring a physiological variable; and a connector for attaching the sensor cover to a sensor;

wherein the connector comprises of one or more attachment arms.

13. The sensor cover of claim 12, wherein the opaque portion is made of a sound-deadening material, the sound-deadening material configured to prevent the sensing portion of the sensor from measuring sound waves.

14. The sensor cover of claim 12, wherein the opaque portion is made of an insulating material, the insulating material configured to prevent the sensing portion of the sensor from measuring electrical signals.

15. The sensor cover of claim 12, wherein the sensor is a clip-type sensor.

16. A sensor cover for use with a noninvasive physiological sensor, the sensor cover comprising:

an opaque portion attachable over a sensing portion of the sensor, the opaque portion preventing the sensing portion from measuring a physiological variable;

a connector for attaching the sensor cover to a sensor; and one or more conductive leads disposed on the opaque portion, the conductive leads configured to generate a short circuit in the sensor.

17. A sensor cover for use with a noninvasive physiological sensor, the sensor cover comprising:

an opaque portion attachable over a sensing portion of the sensor, the opaque portion preventing the sensing portion from measuring a physiological variable; and a connector for attaching the sensor cover to a sensor;

wherein the sensor is an adhesive sensor having a flexible substrate and an adhesive layer;

wherein the opaque portion is an elongate protrusion integrated with the flexible substrate, wherein the connector is slot disposed on the flexible substrate for receiving the protrusion, and wherein placing the protrusion within the slot attaches the protrusion over the sensing portion.

* * * * *